United States Patent
Cao et al.

(10) Patent No.: US 7,901,664 B2
(45) Date of Patent: Mar. 8, 2011

(54) SYNTHESIS OF ALUMINOPHOSPHATE AND METALLOALUMINOPHOSPHATE MOLECULAR SIEVES

(75) Inventors: Guang Cao, Branchburg, NJ (US); Mobae Afeworki, Lopatcong Township, NJ (US); Matu J. Shah, Hackettstown, NJ (US); Machteld Maria Mertens, Boortmeerbeek (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 465 days.

(21) Appl. No.: 12/059,178

(22) Filed: Mar. 31, 2008

(65) Prior Publication Data

US 2009/0247802 A1  Oct. 1, 2009

(51) Int. Cl.
*C01B 39/04* (2006.01)
*C01B 39/54* (2006.01)
*C07C 1/20* (2006.01)

(52) U.S. Cl. ......... 423/705; 423/706; 423/707; 423/305; 423/306; 423/DIG. 30; 585/640; 502/60

(58) Field of Classification Search .............. 423/705, 423/706, 707, 305, 306, DIG. 30; 585/640; 502/60
See application file for complete search history.

(56) References Cited

U.S. PATENT DOCUMENTS

| 3,766,093 A | 10/1973 | Chu |
| 6,812,372 B2 | 11/2004 | Janssen et al. |
| 2003/0231999 A1 | 12/2003 | Cao et al. |
| 2003/0232006 A1 | 12/2003 | Cao et al. |
| 2003/0232718 A1 | 12/2003 | Cao et al. |
| 2004/0253163 A1 | 12/2004 | Cao et al. |
| 2005/0009691 A1 | 1/2005 | Cao et al. |

FOREIGN PATENT DOCUMENTS

| EP | 0 391 774 | 10/1990 |
| WO | WO 03/106341 | 12/2003 |
| WO | WO 2005/115969 | 12/2005 |
| WO | 2008/033229 | 3/2008 |

OTHER PUBLICATIONS

ST Wilson, "Synthesis of AlPO4-based Molecular Sieves", Studies in Surface Science and Catalysis Series, Introduction of Zeolita Science and Practice, vol. 58, 1991, pp. 137-151.

*Primary Examiner* — David M Brunsman
(74) *Attorney, Agent, or Firm* — David M. Weisberg

(57) ABSTRACT

In a method of synthesizing an aluminophosphate or metalloaluminophosphate molecular sieve, a synthesis mixture is provided comprising water, a source of aluminum, a source of phosphorus, optionally a source of a metal other than aluminum, a tertiary amine, and an alkylating agent capable of reacting with said tertiary amine to form a quaternary ammonium compound capable of directing the synthesis of said molecular sieve. The synthesis mixture is maintained under conditions sufficient to cause the alkylating agent to react with the tertiary amine to produce the quaternary ammonium compound and to induce crystallization of the molecular sieve.

37 Claims, 5 Drawing Sheets

Figure 1(a)                    Figure 1(b)
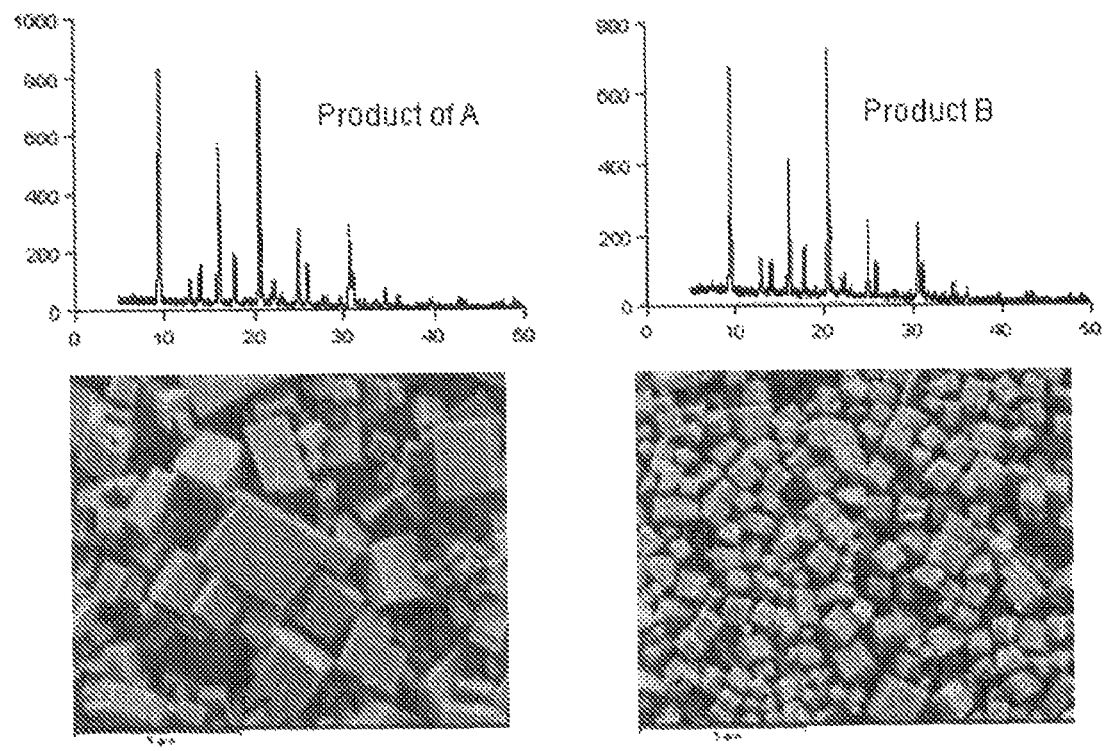
Figure 2(a)                    Figure 2(b)

SYNTHESIS OF ALUMINOPHOSPHATE AND METALLOALUMINOPHOSPHATE MOLECULAR SIEVES

FIELD OF THE INVENTION

This invention relates to the synthesis of aluminophosphate and metalloaluminophosphate molecular sieves.

BACKGROUND OF THE INVENTION

Aluminophosphate and metalloaluminophosphate molecular sieves, particularly silicoaluminophosphate (SAPO) molecular sieves, exhibit a wide range of framework types and are useful as catalysts in a variety of reactions. Of particular interest are the CHA framework type materials, such as SAPO-34, and the AEL framework type materials, such as SAPO-11 (see "Atlas of Zeolite Framework Types", 2007, 6th Revised Edition). Thus CHA framework type molecular sieves have shown particular activity and selectivity in the conversion of oxygenates, such as methanol, to olefins, especially ethylene and propylene. Similarly, it is known that SAPO-11 molecular sieves catalyze hydroisomerization reactions of wax with high selectivity yielding lubricants with high viscosity index and low pore point. SAPO-11 has also been found to be useful as a catalyst in naphtha cracking where it is found to give a high selectivity for propylene. Intergrowths of different framework type molecular sieves have also shown considerable promise as catalytic materials, for example intergrowths of CHA and AEI framework type materials, such as EMM-2, have been found to be highly attractive catalysts for the conversion of oxygenates to olefins (see, for example, U.S. Pat. No. 6,812, 372).

The synthesis of aluminophosphate and metalloaluminophosphate molecular sieves is normally conducted by initially producing a synthesis mixture comprising water, an organic template, typically a nitrogen containing organic base, such as a quaternary ammonium salt or hydroxide, an aluminum oxide, phosphoric acid and optionally a source of silicon or other metal. The resulting gel mixture is then subjected to hydrothermal conditions in a sealed vessel to induce crystallization. The crystalline product is then recovered by filtration or centrifugation.

The organic template, which is sometimes referred to as a structure directing agent because of its role in determining the framework type of the molecular sieve product, also plays the role of moderating the pH of the synthesis gel mixture. However, the organic template, particularly where the template is a quaternary ammonium compound, is frequently the most costly ingredient used in the synthesis mixture. There is therefore significant interest in finding improved and less expensive templating systems for the production of aluminophosphate and metalloaluminophosphate molecular sieves. For example, in the case of CHA framework type silicoaluminophosphates, triethylamine, tetraethylammonium hydroxide (TEAOH) and morpholine have all been found to be suitable templating agents.

More recently, in U.S. Patent Application Publication Nos. 2003/0231999, 2003/0232006, and 2003/0232718, we have shown that CHA framework type aluminophosphates and silicoaluminophosphates can be synthesized in the presence of at least one template containing one or more N,N-dimethylamino moieties having the structure $(CH_3)_2N$—R wherein R linear or branched alkyl group, a linear or branched alcohol, or a linear or branched amine. Suitable templates include, but are not limited to N,N-dimethylethanolamine, N,N-dimethylbutanolamine, N,N-dimethylheptanolamine, N,N-dimethylhexanol-amine, N,N-dimethylethylenediamine, N,N-dimethylpropyelenediamine, N,N-dimethylbutylenediamine, N,N-dimethylheptylenediamine, N,N-dimethyl-hexylenediamine, dimethylethylamine, dimethylpropylamine, dimethylheptyl-amine and dimethylhexylamine.

In addition, U.S. Patent Application Publication No. 2004/0253163 discloses the synthesis of silicoaluminophosphate molecular sieves having the CHA framework type employing a directing agent having the formula:

wherein $R^1$ and $R^2$ are independently selected from the group consisting of alkyl groups having from 1 to 3 carbon atoms and hydroxyalkyl groups having from 1 to 3 carbon atoms and $R^3$ is selected from the group consisting of 4- to 8-membered cycloalkyl groups, optionally substituted by 1 to 3 alkyl groups having from 1 to 3 carbon atoms; and 4- to 8-membered heterocyclic groups having from 1 to 3 heteroatoms, said heterocyclic groups being optionally substituted by 1 to 3 alkyl groups having from 1 to 3 carbon atoms and the heteroatoms in said heterocyclic groups being selected from the group consisting of O, N, and S. Preferably, the directing agent is selected from N,N-dimethyl-cyclohexylamine, N,N-dimethyl-methylcyclohexylamine, N,N-dimethyl-cyclopentylamine, N,N-dimethyl-methyl-cyclopentylamine, N,N-dimethyl-cycloheptylamine, N,N-dimethyl-methylcycloheptylamine, and most preferably is N,N-dimethyl-cyclohexylamine.

U.S. Pat. No. 3,766,093 discloses synthesis of the aluminosilicate zeolite ZSM-5 in the presence of tetrapropylammonium hydroxide (Example 1) and in the presence of a mixture of tri-n-propylamine and n-propyl bromide (Examples 3 and 4).

However, while trialkylamines are generally less expensive than their quaternary ammonium counterparts, the latter exhibit some advantages over amines in the areas of improved control of acid site density, acid site distribution and crystal size of the resultant molecular sieve. According to the present invention it has now been found that the advantages of quaternary ammonium compounds in molecular sieve synthesis can be achieved without their concomitant cost disadvantage by producing the quaternary ammonium compounds in situ in the synthesis mixture by reaction between a tertiary amine and an alkylating agent, especially an alkyl phosphate. When an alkyl phosphate is employed as the alkylating agent for, the alkyl phosphate not only converts the trialkylamine into a quaternary ammonium compound but also provides a source of phosphate for the synthesis. In this way, the amount of phosphoric acid added to the synthesis mixture can be reduced, so that the initial pH of the gel tends to be higher, which favors the dispersion of the silicon in the resulting crystalline product.

SUMMARY OF THE INVENTION

Accordingly, the invention resides in one aspect in a method of synthesizing an aluminophosphate or metalloaluminophosphate molecular sieve, the method comprising:

(a) providing a synthesis mixture comprising water; a source of aluminum; a source of phosphorus; optionally a source of a metal other than aluminum; a tertiary amine; and an alkylating agent capable of reacting with said tertiary amine to form a quaternary ammonium compound capable of directing the synthesis of said molecular sieve; and (b) maintaining said synthesis mixture under conditions sufficient to cause said alkylating agent to react with said tertiary amine to produce said quaternary ammonium compound and to induce crystallization of said molecular sieve.

Conveniently, said alkylating agent provides at least part of said source of phosphorus in the synthesis mixture. In one embodiment, said alkylating agent comprises an alkyl phosphate, such as a trialkyl phosphate.

In a further aspect, the invention resides in a method of synthesizing an aluminophosphate or metalloaluminophosphate molecular sieve, the method comprising:

(a) providing a synthesis mixture comprising water; a source of aluminum; an amine of the formula $R^1R^2R^3N$ where each of $R^1$, $R^2$, and $R^3$ is independently an alkyl group or hydroxyalkyl group having from 1 to 8 carbon atoms; a trialkyl phosphate of the formula $(R^4O)_3P=O$ where each $R^4$ is an alkyl group having from 1 to 4 carbon atoms, and optionally a source of a metal other than aluminum; and (b) maintaining said synthesis mixture under conditions sufficient to cause said trialkyl phosphate to react with said amine to produce a quaternary ammonium compound and to induce crystallization of said molecular sieve.

In one embodiment, each of $R^1$, $R^2$, and $R^3$ is independently a linear or branched alkyl group having from 1 to 4 carbon atoms. Conveniently, said amine comprises triethylamine.

In another embodiment, $R^1$ and $R^2$ are independently selected from alkyl and hydroxyalkyl groups having from 1 to 3 carbon atoms and $R^3$ is selected from 4- to 8-membered cycloalkyl groups optionally substituted by 1 to 3 alkyl groups having from 1 to 3 carbon atoms. Conveniently, said amine comprises N,N-dimethylcyclohexylamine.

In one embodiment, each $R^4$ is a linear or branched alkyl group having from 1 to 4 carbon atoms. Conveniently, the trialkylphosphate comprises triethylphosphate.

Conveniently, the molar ratio of amine to trialkylphosphate in the synthesis mixture is at least 3.

Typically, the synthesis mixture comprises a source of silicon and/or a source of phosphorus in addition to said trialkylphosphate. Conveniently, the synthesis mixture also contains seeds.

In yet a further aspect, the invention resides in a catalyst composition comprising a crystalline aluminophosphate or silicoaluminophosphate molecular sieve including a CHA framework-type material produced by the method described herein.

In yet a further aspect, the invention resides in a process for producing olefins comprising contacting an organic oxygenate compound under oxygenate conversion conditions with the catalyst composition described herein.

BRIEF DESCRIPTION OF THE DRAWINGS

FIGS. 1(a) and 1(b) are X-ray diffraction patterns of the as-synthesized products A and B of Example 1.

FIGS. 2(a) and 2(b) are scanning electron micrographs of the as-synthesized products A and B of Example 1.

DETAILED DESCRIPTION OF THE PREFERRED EMBODIMENTS

Figure 3:
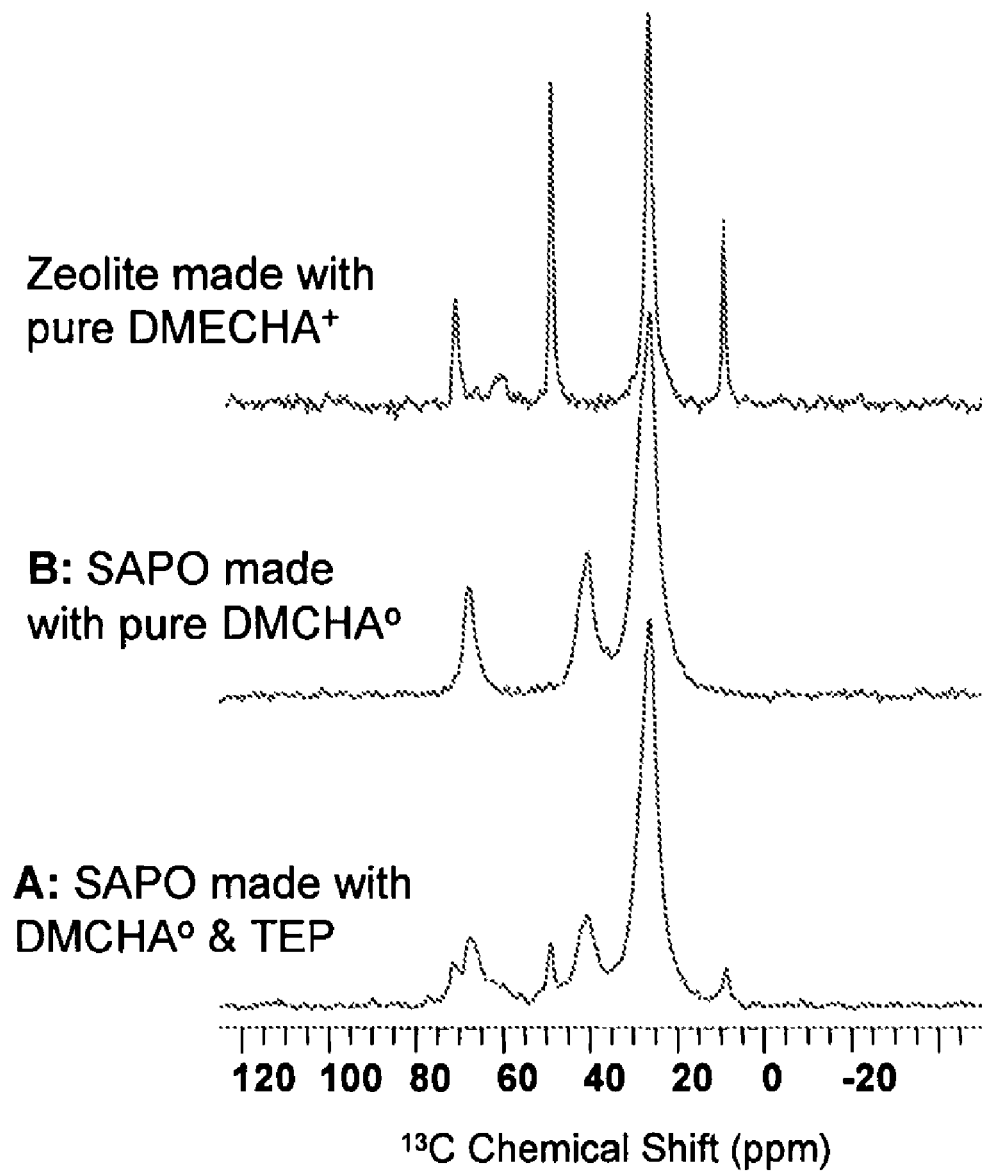
FIG. 3 compares the $^{13}$C MAS NMR spectra of the as-synthesized products A and B of Example 1 with the $^{13}$C MAS NMR spectrum of a CHA framework-type zeolite produced using pre-prepared N,N,N-dimethylethyl-cyclohexylammonium (DMECHA) cations as the directing agent.

Described herein is a method of synthesizing an aluminophosphate or metalloaluminophosphate molecular sieve from a synthesis mixture comprising water; a source of aluminum; a source of phosphorus; optionally a source of a metal other than aluminum; a tertiary amine; and an alkylating agent capable of reacting with the tertiary amine to form a quaternary ammonium compound capable of directing the synthesis of said molecular sieve. The synthesis mixture is maintained under conditions sufficient to cause the alkylating agent to react with the tertiary amine to produce the quaternary ammonium directing agent and to induce crystallization of said molecular sieve. Thus, in the present process the quaternary ammonium compound required to direct the crystallization of the desired molecular sieve is produced in situ in the crystallization step.

Although the tertiary amine employed in the present process is not closely controlled, suitable amines are typically those of the formula (I)

$$R^1R^2R^3N \qquad (I)$$

where each of $R^1$, $R^2$, and $R^3$ is independently an alkyl group or hydroxyalkyl group having from 1 to 8 carbon atoms. In a first embodiment, each of $R^1$, $R^2$, and $R^3$ is independently a linear or branched alkyl group having from 1 to 4 carbon atoms. Conveniently, the amine of the first embodiment comprises triethylamine. In a second embodiment, $R^1$ and $R^2$ are independently selected from alkyl and hydroxyalkyl groups having from 1 to 3 carbon atoms and $R^3$ is selected from 4- to 8-membered cycloalkyl groups optionally substituted by 1 to 3 alkyl groups having from 1 to 3 carbon atoms. Conveniently, the amine of the second embodiment comprises N,N-dimethylcyclohexylamine.

Similarly, any alkylating agent capable of reacting with a tertiary amine under conditions suitable to induce crystallization of aluminophosphates and metalloaluminophosphates can be employed in the present process. It is, however, particularly desirable to employ an alkylating agent that provides at least part of said source of phosphorus in the synthesis mixture. In fact, in one embodiment, the alkylating agent can provide all or substantially all (i.e., at least 98%, preferably at least 99%, for example at least 99.5%, at least 99.9%, or at least 99.99%, by weight) of said source of phosphorus in the synthesis mixture. In another embodiment, the alkylating agent can provide less than 85 wt %, preferably less than 75 wt %, for example less than 65 wt %, less than 60 wt %, less than 55 wt %, less than 50 wt %, less than 45 wt %, or less than 40 wt % of said source of phosphorus in the synthesis mixture. Suitable alkylating agents therefore comprise alkyl phosphate, such as trialkyl phosphates of the formula (II)

$$(R^4O)_3P=O \qquad (II)$$

where each $R^4$ is an alkyl group having from 1 to 4 carbon atoms, especially an ethyl group. In such a case, the in situ alkylation reaction to produce the quaternary ammonium directing agent is as follows:

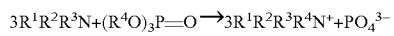

$$3R^1R^2R^3N + (R^4O)_3P=O \rightarrow 3R^1R^2R^3R^4N^+ + PO_4^{3-}$$

Because trialkylamines are usually much less expensive than their corresponding quaternary ammonium hydroxides, and the ethyl version of the trialkylphosphate is a low-cost bulk chemical, their use in the above reaction provides a lower cost synthesis route than conventional methods employed pre-formed quaternary ammonium compounds. Furthermore, because the by-product is phosphate anion, the reaction essentially replaces the expensive combination of quaternary ammonium hydroxide and phosphoric acid with trialkylamine and trialkylphosphate, which can produce in situ a substantially similar quaternary ammonium phosphate as can be used in a conventional gel mixture. The trialkylphosphate as an in-situ reagent can be used as both an alkylating agent and a source of phosphate.

The amine/phosphate combination used in the above reaction can provide an additional control in the crystallization process in that, because trialkylphosphate can replace at least some of the phosphoric acid used in the synthesis gel, the initial pH of the gel can tend to be higher. The higher pH favors the dispersion of silicon in the resulting crystal and so is less likely to result in Si-islanding.

Although the use of a phosphorus-containing alkylating agent can provide the sole source of phosphorus in the synthesis mixture, in many cases one or more additional sources of phosphorus will also be present. Generally, the additional source of phosphorus can be a phosphoric acid, especially orthophosphoric acid, but other sources, for example, organic phosphates such as triethylphosphate and/or aluminophosphates may also be used.

Suitable sources of aluminum for use in the present synthesis mixture are typically those known in the art or as described in the literature for the production of the aluminophosphate or metalloaluminophosphate concerned. Thus the aluminum source may, for example, be an aluminum oxide (alumina), optionally hydrated, an aluminum salt, especially a phosphate, an aluminate, or a mixture thereof. A preferred source includes a hydrated alumina, most preferably a pseudoboehmite, which contains about 75% $Al_2O_3$ and 25% $H_2O$ by weight.

Where a source of a metal other than aluminum is present ion the synthesis metal, this other metal normally comprises, or is, silicon. Suitable sources of silicon can include, but are not limited to, silica, for example colloidal silica, fumed silica, or an organic silicon source, e.g., a tetraalkyl orthosilicate, especially tetraethyl orthosilicate.

Suitable conditions for effecting both in situ production of the desired quaternary ammonium directing agent and crystallization of the molecular sieve generally include a temperature from about 120° C. to about 220° C. for a time of about 4 hours to about 240 hours. In some cases, synthesis of the desired (metallo) aluminophosphate molecular sieve may be facilitated by the presence of between about 0.01 ppm by weight (wppm) and about 10,000 wppm, typically between about 100 wppm to about 5,000 wppm, of seeds crystals either of the same or a different molecular sieve. When crystallization is complete, the resultant molecular sieve can be separated from the mother liquor and recovered, such as by centrifugation or filtration, washed and dried.

As a result of the crystallization process, the recovered molecular sieve generally contains within its pores at least a portion of the quaternary ammonium directing agent formed in situ in the synthesis. Thus, prior to use as a catalyst or sorbent, the as-synthesized product is normally "activated" by partial or complete removal of the organic directing agent from the molecular sieve, e.g., leaving unobstructed pores and catalytically active sites within the microporous channels of the molecular sieve open for contact with a feedstock. The activation process is typically accomplished by calcining, or essentially heating the molecular sieve comprising the template at a temperature from about 200° C. to about 800° C., typically in the presence of an oxygen-containing gas.

It will be appreciated that, depending on the composition of the alkylating agent and the tertiary amine, the present process can be employed to produce aluminophosphate and metalloaluminophosphate molecular sieves having a wide variety of framework types. By way of example, when the alkylating agent is triethylphosphate and the trialkylamine is triethylamine, the process can be used to produce molecular sieves comprising a CHA framework type material, including molecular sieves comprising intergrowths of CHA and AEI framework type materials. Similarly, CHA framework type-containing materials can be produced when the alkylating agent is triethylphosphate and the trialkylamine is N,N-dimethylcyclohexylamine.

The aluminophosphate and metalloaluminophosphate molecular sieves produced by the present method can be used, inter alia, to dry gases and liquids; for selective molecular separation based on size and polar properties; as ion-exchangers; as chemical carriers; in gas chromatography; and as catalysts in organic conversion reactions. Examples of suitable catalytic uses of the molecular sieves produced by the present method can include, but are not limited to, (a) hydrocracking of heavy petroleum residual feedstocks, cyclic stocks and other hydrocrackate charge stocks, normally in the presence of a hydrogenation component selected from Groups 6 and 8-10 of the Periodic Table of Elements; (b) dewaxing, including isomerization dewaxing, to selectively remove (straight chain) paraffins from hydrocarbon feedstocks typically boiling above 177° C., including raffinates and lubricating oil basestocks; (c) catalytic cracking of hydrocarbon feedstocks, such as naphthas, gas oils and residual oils, normally in the presence of a large pore cracking catalyst, such as zeolite Y; (d) oligomerization of straight and branched chain olefins having from about 2 to 21, preferably 2 to 5 carbon atoms, to produce medium to heavy olefins which are useful for both fuels, i.e., gasoline or a gasoline blending stock, and chemicals; (e) isomerization of olefins, particularly olefins having 4 to 6 carbon atoms, and especially normal butene to produce iso-olefins; (f) upgrading of lower alkanes, such as methane, to higher hydrocarbons, such as ethylene and benzene; (g) disproportionation of alkylaromatic hydrocarbons, such as toluene, to produce dialkylaromatic hydrocarbons, such as xylenes; (h) alkylation of aromatic hydrocarbons, such as benzene, with olefins, such as ethylene and propylene to produce ethylbenzene and cumene; (i) isomerization of dialkylaromatic hydrocarbons, such as xylenes, (j) catalytic reduction of nitrogen oxides and (k) synthesis of monoalkylamines and dialkylamines.

Where the molecular sieve produced by the present method comprises a CHA framework-type material, the molecular sieve is found to be particularly useful as a catalyst in the conversion of oxygenates to one or more olefins, particularly ethylene and propylene.

As used herein, the term "oxygenates" is defined to include, but is not necessarily limited to, aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety normally contains from 1 to 10 carbon atoms, such as from 1 to 4 carbon atoms.

Representative oxygenates include, without limitation, lower straight chain or branched aliphatic alcohols, their unsaturated counterparts, and their nitrogen, halogen, and sulfur analogues. Examples of suitable oxygenate compounds include, but are not limited to; methanol; ethanol; n-propanol; isopropanol; $C_4$ to $C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range from 3 to 10 carbon atoms; and mixtures thereof. Particularly suitable oxygenate compounds are methanol, dimethyl ether, or mixtures thereof, most preferably containing some methanol. As used herein, the term "oxygenate," in reference to feed in an oxygenate conversion process, designates only the organic material used as the feed. The total charge of feed to the reaction zone may contain additional compounds, such as diluents.

In such an oxygenate conversion process, a feedstock comprising an organic oxygenate, optionally with one or more diluents, can be contacted in the vapor phase in a reaction zone with a catalyst comprising the present molecular sieve at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result, depending upon the catalyst and the reaction conditions.

When present, the diluent(s) is (are) generally non-reactive to the feedstock or molecular sieve catalyst composition and is (are) typically used to reduce the concentration of the oxygenate in the feedstock. Non-limiting examples of suitable diluents can include helium, argon, nitrogen, carbon monoxide, carbon dioxide, water, essentially non-reactive paraffins (especially alkanes such as methane, ethane, and propane), essentially non-reactive aromatic compounds, and mixtures thereof, inter alia. The most preferred diluents include water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example from about 250° C. to about 800° C., including from about 250° C. to about 750° C., conveniently from about 300° C. to about 650° C., typically from about 350° C. to about 600° C., and particularly from about 400° C. to about 600° C.

Light olefin products will form, although not necessarily in optimum amounts, at a wide range of pressures, including but not limited to autogenous pressures and pressures in the range from about 0.1 kPa to about 10 MPa. Conveniently, the pressure can be in the range from about 7 kPa to about 5 MPa, such as from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

A wide range of weight hourly space velocities (WHSV) for the feedstock will function in the oxygenate conversion process. WHSV is defined as weight of feed (excluding diluent) per hour per weight of a total reaction volume of molecular sieve catalyst (excluding inerts and/or fillers). The WHSV generally should be in the range from about $0.01\ hr^{-1}$ to about $500\ hr^{-1}$, such as from about $0.5\ hr^{-1}$ to about $300\ hr^{-1}$, for example from about $0.1\ hr^{-1}$ to about $200\ hr^{-1}$.

A practical embodiment of a reactor system for the oxygenate conversion process is a circulating fluid bed reactor with continuous regeneration, similar to a modern fluid catalytic cracker. Fixed beds are generally not preferred for the process because oxygenate to olefin conversion is a highly exothermic process, which requires several stages with intercoolers or other cooling devices. The reaction also typically results in a high pressure drop, due to the production of low pressure, low density gas.

Additionally or alternately, the invention can be described by the following embodiments.

Embodiment 1

A method of synthesizing an aluminophosphate or metalloaluminophosphate molecular sieve, the method comprising: (a) providing a synthesis mixture comprising water; a source of aluminum; a source of phosphorus; optionally a source of a metal other than aluminum; a tertiary amine; and an alkylating agent capable of reacting with said tertiary amine to form a quaternary ammonium compound capable of directing the synthesis of said molecular sieve; and (b) maintaining said synthesis mixture under conditions sufficient to cause said alkylating agent to react with said tertiary amine to produce said quaternary ammonium compound and to induce crystallization of said molecular sieve.

Embodiment 2

The method of embodiment 1, wherein said alkylating agent comprises at least part of said source of phosphorus.

Embodiment 3

The method of either of embodiments 1 or 2, wherein said alkylating agent comprises an alkyl phosphate, preferably a trialkyl phosphate.

Embodiment 4

A method of synthesizing an aluminophosphate or metalloaluminophosphate molecular sieve, the method comprising: (a) providing a synthesis mixture comprising water; a source of aluminum; an amine of the formula $R^1R^2R^3N$, where each of $R^1$, $R^2$, and $R^3$ is independently an alkyl group or hydroxyalkyl group having from 1 to 8 carbon atoms; a trialkyl phosphate of the formula $(R^4O)_3P=O$, where each $R^4$ is an alkyl group having from 1 to 4 carbon atoms, and optionally a source of a metal other than aluminum; and (b) maintaining said synthesis mixture under conditions sufficient to cause said trialkyl phosphate to react with said amine to produce a quaternary ammonium compound and to induce crystallization of said molecular sieve.

Embodiment 5

The method of embodiment 4, wherein each of $R^1$, $R^2$, and $R^3$ is independently a linear or branched alkyl group having from 1 to 4 carbon atoms, and preferably each is ethyl.

Embodiment 6

The method of embodiment 4, wherein $R^1$ and $R^1$ are independently selected from alkyl and hydroxyalkyl groups having from 1 to 3 carbon atoms and $R^3$ is selected from 4- to 8-membered cycloalkyl groups optionally substituted by 1 to 3 alkyl groups having from 1 to 3 carbon atoms, and preferably said amine comprises N,N-dimethylcyclohexylamine.

Embodiment 7

The method of any one of embodiments 4 to 6, wherein each $R^4$ is a linear or branched alkyl group having from 1 to 4 carbon atoms, and preferably each is ethyl.

Embodiment 8

The method of any one of embodiments 4 to 7, wherein the amine and trialkylphosphate are present in the synthesis mixture in a molar ratio of at least 3:1.

Embodiment 9

The method of any one of embodiments 4 to 8, wherein the synthesis mixture comprises a source of phosphorus, preferably phosphoric acid, in addition to said trialkyl phosphate.

Embodiment 10

The method of any preceding embodiment, wherein the synthesis mixture comprises a source of silicon as the source of the metal other than aluminum.

Embodiment 11

The method of any preceding embodiment, wherein the synthesis mixture also contains seeds, preferably from 0.01 wppm to 10,000 wppm of seeds, and more preferably from 100 wppm to 5,000 wppm of seeds.

Embodiment 12

The method of any preceding embodiment, wherein said conditions include a temperature from 120° C. to 220° C. for a time from 4 hours to 240 hours.

Embodiment 13

The method of any preceding embodiment, wherein said molecular sieve comprises a CHA framework type material.

Embodiment 14

A catalyst composition comprising a crystalline aluminophosphate or silicoaluminophosphate molecular sieve including a CHA framework-type material produced by the method of any preceding embodiment.

Embodiment 15

A process for producing olefins comprising contacting an organic oxygenate compound under oxygenate conversion conditions with the catalyst composition of embodiment 14.

The invention will now be more particularly described with reference to the following non-limiting Examples.

EXAMPLES

In the Examples, X-ray Powder Diffractograms were recorded on either a Stöe Stadi-P Combi transmission X-ray Diffractometer with CuK-alpha radiation or a Bruker axs D4 diffractometer with voltage of 35 kV and current of 45 mA, using Cu target and Ni-filter ($\lambda$=0.154 nm). Elemental analysis of Al, Si, and P was performed using Inductively Coupled Plasma (ICP) spectroscopy.

Example 1

Synthesis of SAPO—CHA with
N,N-dimethylcyclohexylamine (DMCHA) and
triethylphosphate (TEP)

The following ingredients were mixed, in sequence, into a uniform gel: distilled water, 56 wt % $H_3PO_4$ (diluted from 85% $H_3PO_4$ which was obtained from Aldrich Chemical Company—for molar ratio purposes, this component is represented in its oxide form, as $P_2O_5$), Condea Pural SB (pseudoboehmite, 74.2 wt % $Al_2O_3$, available from Condea Vista Company, Texas, USA), Ludox AS40 (available from Aldrich, USA), and then DMCHA and TEP. Finally a colloidal SAPO-34 seed suspension (containing 6.6 wt % solid) was added in an amount that corresponded to 100 ppm seeds with regard to gel weight. The molar ratio of the ingredients in this gel (A) was as follows:

(A) 2.0 DMCHA:1.0 $Al_2O_3$:0.2 $SiO_2$:0.5 TEP:0.75 $P_2O_5$: $40H_2O$

Another gel was prepared in essentially the same way, except that TEP was not added and the silicon source was tetraethylorthosilicate (TEOS). The gel composition was as follows:

(B) 2.0 DMCHA:1.0 $Al_2O_3$:0.2 $SiO_2$:1.0 $P_2O_5$:40 $H_2O$

The synthesis mixtures were sealed in autoclaves and heated to about 170° C. without agitation. Heating was stopped after about 72 hours, and the solid products were purified by repeated water washing with centrifugation/removing supernatant cycles. The washed products were finally dried in a vacuum oven before subsequent analyses.

XRD patterns of both products showed that both were SAPO with predominantly CHA character. The XRD patterns and the SEM micrographs are shown in FIGS. 1 and 2 respectively. Yields of products A and B were about 16.1 wt % and 14.5 wt %, respectively, with regard to gel weight. Elemental analysis results are as follows:

| Product A: | Composition by weight: | 16.8% Al, 1.69% Si, 17.9% P Anhydrous |
|---|---|---|
| | molar composition: | $Al_{1.00}Si_{0.097}P_{0.928}$ |
| Product B: | Composition by weight: | 16.8% Al, 2.20% Si, 17.2% P; |
| | Anhydrous molar composition: | $Al_{1.00}Si_{0.126}P_{0.892}$ |

The presence of the N,N,N-dimethylethylcyclohexylammonium (DMECHA) cation in the crystalline product A was evidenced by solid-state $^{13}C$ NMR spectroscopy, as shown in FIG. 3. The $^{13}C$ MAS NMR spectra were acquired at a spinning speed of 8-kHz using a $^{13}C$ 90-degree pulse, followed by signal acquisition and a 60-s recycle delay. Protons were decoupled during data acquisition. Whereas the as-synthesized product B showed the expected $^{13}C$ resonances from DMCHA (three groups of peaks) in the spectrum, product A showed additional peaks identical in both chemical shift and relative peak intensity to a DMECHA-templated high-silica zeolite having the chabazite framework type (spectrum also shown in FIG. 3 for comparison). The relative amounts of DMECHA can be calculated from the NMR spectra, because distinct resonances that belong only to DMECHA are observed.

This example shows that a trialkylamine can be alkylated by trialkylphosphate in-situ during hydrothermal synthesis, thereby producing a quaternary ammonium compound as a structure directing agent. The chemical reaction taking place is believed to be as follows:

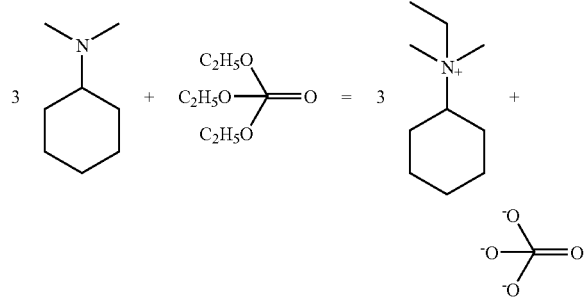

Example 2

Synthesis of SAPO—CHA with triethylamine (TEA) and triethylphosphate (TEP)

The following ingredients were mixed, in sequence, and blended into a relatively uniform gel using a microhomogenizer (Tissue Tearor Model 98730, available from Biospec Products, Inc., USA): 85 wt % $H_3PO_4$ (obtained from Aldrich Chemical Company—for molar ratio purposes, this component is represented in its oxide form, as $P_2O_5$), $H_2O$, Catapal™ A (74 wt % $Al_2O_3$, available from CONDEA Vista Company, Texas, USA), Cabosil™ (available from Cabot Corporation, Illinois, USA), and then triethylamine and triethylphosphate. The molar ratio of the ingredients was as follows:
(C-1 & C-2) 2.0 TEA:1.0 $Al_2O_3$:0.15 $SiO_2$:0.5 TEP:0.75 $P_2O_5$:40 $H_2O$
(D-1 & D-2) 1.5 TEA:1.0 $Al_2O_3$:0.15 $SiO_2$:0.5 TEP:0.75 $P_2O_5$:40 $H_2O$
(E-1 & E-2) 1.0 TEA:1.0 $Al_2O_3$:0.15 $SiO_2$:0.5 TEP:0.75 $P_2O_5$:40 $H_2O$ Each of these gels was divided into two approximately equal portions. To portions C-1, D-1, and E-1 were added 200 ppm colloidal SAPO-34 seeds while no seeds were added to portions C-2, D-2, and E-2. These gels were then sealed in Teflon-lined stainless steel autoclaves. The autoclaves were placed in an oven that was heated to about 170° C., and were tumbled on a rotating rack at approximately 40 rpm. The autoclaves were taken out of the oven after about 3 days. After quench cooling of the bombs with running tap water, the contents of the autoclaves were centrifuged, and the solid washed several times with deionized water, until the conductivity of the washing liquid was below about 50 μS/cm. The solids were dried at about 60° C. in a vacuum oven overnight.

TABLE 1

| Sample | Phase Identification | Yield (wt %) | Al (%) | Si (%) | P (%) | Molar Composition |
|---|---|---|---|---|---|---|
| C-1 | AEI/CHA Intergrowth, AEI phase <50% | 12.1 | 18.3 | 2.65 | 18.2 | $Al_{1.00}Si_{0.139}P_{0.866}$ |
| C-2 | AEI/CHA Intergrowth, AEI phase <50% | 10.0 | 18.3 | 2.77 | 18.2 | $Al_{1.00}Si_{0.145}P_{0.866}$ |
| D-1 | AEI/CHA Intergrowth, AEI phase ≧40% | 12.6 | 18.0 | 2.23 | 17.8 | $Al_{1.00}Si_{0.119}P_{0.861}$ |
| D-2 | AFI + CHA | 9.6 | — | — | — | — |
| E-1 | AFI + CHA | 13.6 | — | — | — | — |
| E-2 | AFI + trace CHA | 10.6 | — | — | — | — |

Yields, phase identification, and elemental analysis results are shown in Table 1. The yields were calculated as weight percent of the isolated products in the total weight of the initial gel.

These examples indicate that AEI/CHA intergrowths with a range of AEI/CHA phase ratios can be synthesized using an amine in combination with triethylphosphate. The triethylphosphate is believed to alkylate the amine, resulting in the in-situ formation of tetraethylammonium ions, which are also believed to end up templating the products made.

Figure 4:
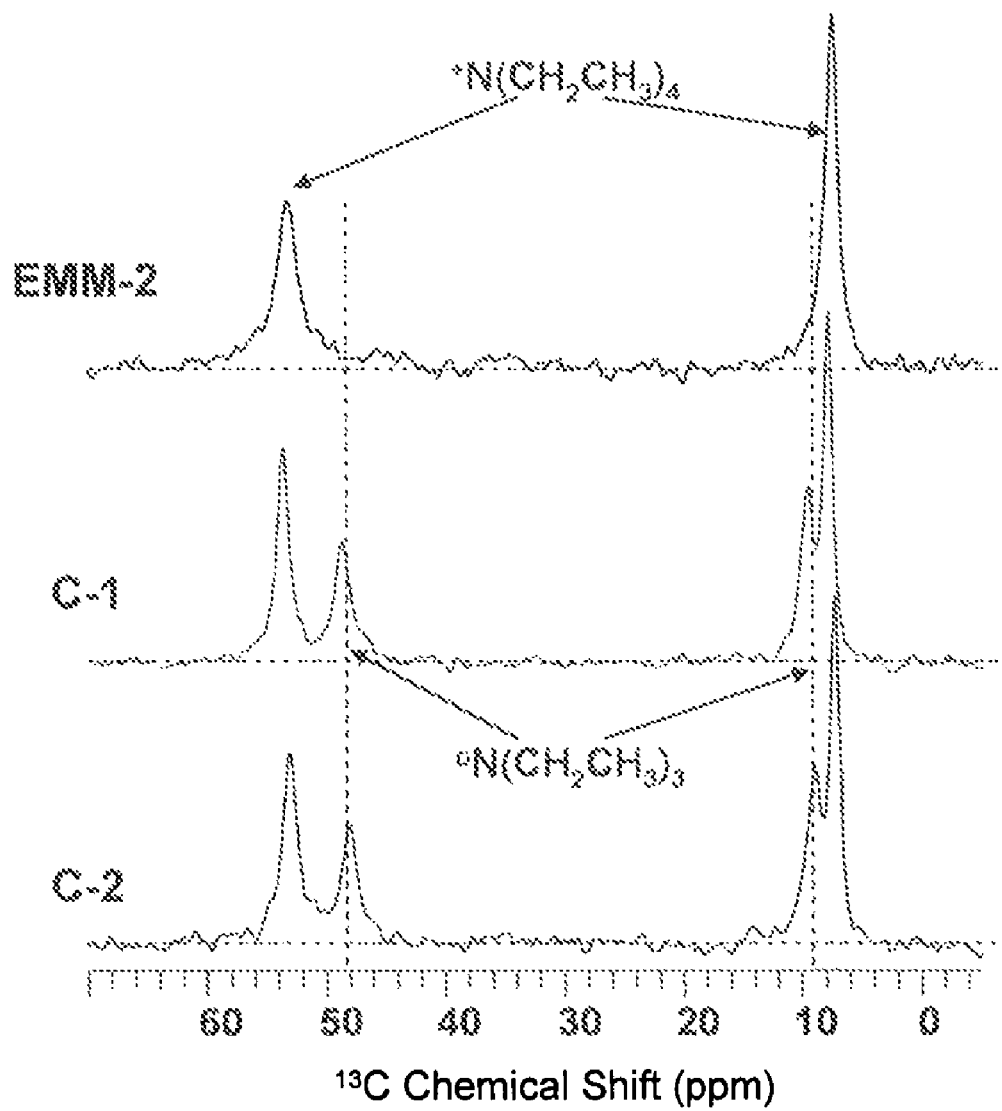
FIG. 4 compares the $^{13}$C MAS NMR spectra of the as-synthesized products C1 and C2 of Example 2 with the $^{13}$C MAS NMR spectrum of an as-synthesized AEI/CHA silicoaluminophosphate intergrowth produced using pre-prepared tetraethylammonium cations as the directing agent.

The presence of tetraethylammonium ion in the as-synthesized final crystalline products was confirmed by solid-state $^{13}C$ NMR spectroscopy. Shown in FIG. 4 are the $^{13}C$ MAS NMR spectra of as-synthesized samples C-1 and C-2 (middle and bottom, respectively), along with the spectrum of an as-synthesized comparative sample of silicoaluminophosphate AEI/CHA intergrowth (made exclusively with pre-prepared tetraethylammonium, $TEA^+$, as template, top). It is clear that, in samples C-1 and C-2, both the neutral amine, triethylamine ($TEA^0$), and the quaternary ammonium ions ($TEA^+$) are occluded in the final crystalline products. The relative ratios (amounts) of $TEA^+$ to $TEA^0$, as calculated from the $^{13}C$ MAS NMR spectra for samples C-1 and C-2, were about 56% and about 50%, respectively.

Example 3

MTO Performance of C-1 and C-2 SAPOs Made with Triethylamine and Triethylphosphate The products C1 and C2 from Example 2 were used to catalyze a methanol-to-olefins reaction in a fixed-bed microreactor. Methanol was fed at a preset pressure and rate to a stainless steel reactor tube housed in an isothermally heated zone. The reactor tube contained about 20 mg weighed and sized granules of the catalyst sample (about 20-40 mesh, by press-and-screen method). The catalyst was activated for about 30 minutes at about 500° C. in flowing nitrogen before methanol was admitted. The product effluent was sampled, at different times during the run, with a twelve-port sampling loop while the catalyst was continuously deactivating. The effluent sample in each port was analyzed with a Gas Chromatograph equipped with an FID detector.

The testing condition was conducted at a temperature of about 475° C. and a methanol pressure of about 40 psia (about 276 kPa). The feed rate in weight hourly space velocity (WHSV) was about 100/hr. Cumulative conversion of methanol was expressed as Cumulative Methanol Conversion (in grams) Per Gram Sieve (CMCPS). On-stream lifetime refers to the CMCPS when methanol conversion has dropped to 10%. The product selectivity was reported as averages over the entire conversion range, rather than from a single point in effluent composition.

Figure 5:
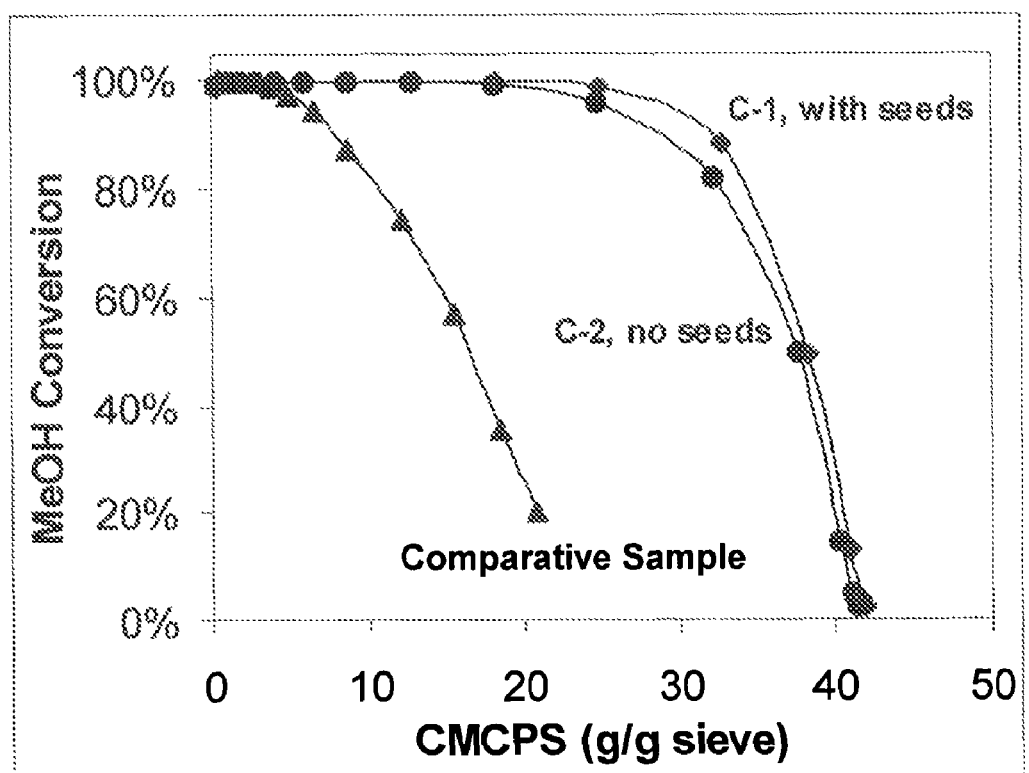
FIG. 5 is a graph comparing the on-stream methanol conversion lifetime for the products C1 and C2 of Example 2 with that of a silicoaluminophosphate AEI/CHA intergrowth produced using pre-prepared tetraethylammonium cations as the directing agent when each is used as a catalyst in the conversion of methanol to olefins according to the process of Example 3.
Figure 6:
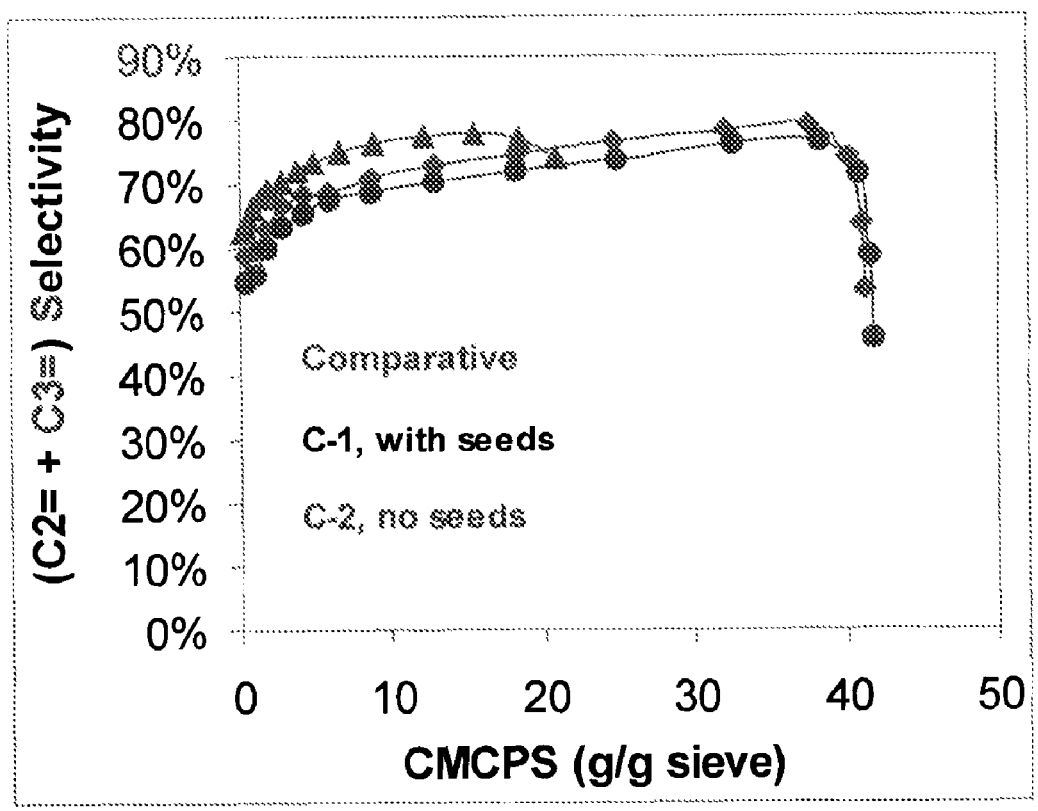
FIG. 6 is a graph comparing light olefin (ethylene+propylene) selectivity against cumulative methanol conversion for the products C1 and C2 of Example 2 with that of a silicoaluminophosphate AEI/CHA intergrowth produced using pre-prepared tetraethylammonium cations as the directing agent when each is used as a catalyst in the conversion of methanol to olefins according to the process of Example 3.

FIGS. 5 and 6 show the conversion and ethylene plus propylene selectivity, respectively, plotted against CMCPS, for samples C-1 and C2, along with those for a comparative silicoaluminophosphate AEI/CHA intergrowth produced from pre-prepared tetraethylammonium ions. Table 2 below lists key product selectivities for the three materials of concern.

TABLE 2

| Sample Description | Ethene and Propene | Ethene to Propene Ratio | $C_2H_4$ | $C_3H_6$ | $CH_4$ | $C_2H_6$ | $C_2H_8$ | $C_3H_8$ | Butenes + Butanes | $C_3^+$ |
|---|---|---|---|---|---|---|---|---|---|---|
| C-1 of Ex. 2 (seeded) | 73.8 | 0.80 | 32.9 | 41.0 | 1.42 | 0.54 | 0.54 | 1.50 | 15.63 | 4.8 |
| C-2 of Ex. 2 (unseeded) | 71.5 | 0.78 | 31.4 | 40.1 | 1.42 | 0.71 | 0.71 | 2.47 | 16.41 | 4.6 |
| EMM-2 (70V-BCT2380) | 74.7 | 0.80 | 33.3 | 41.5 | 1.37 | 0.24 | 0.24 | 0.48 | 15.60 | 5.2 |

The results indicate that the SAPO sieves, prepared by the in-situ formation of quaternary ammonium template as described herein, have roughly twice the on-stream lifetime of a silicoaluminophosphate AEI/CHA intergrowth produced from pre-prepared tetraethylammonium ions. The selectivity for light olefins (ethene and propene) is comparable.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A method of synthesizing an aluminophosphate or metalloaluminophosphate molecular sieve, the method comprising:
   (a) providing a synthesis mixture comprising water; a source of aluminum; a source of phosphorus; optionally a source of a metal other than aluminum; a tertiary amine; and an alkylating agent capable of reacting with said tertiary amine to form a quaternary ammonium compound capable of directing the synthesis of said molecular sieve; and
   (b) maintaining said synthesis mixture under conditions sufficient to cause said alkylating agent to react with said tertiary amine to produce said quaternary ammonium compound and to induce crystallization of said molecular sieve;
   wherein the tertiary amine has the formula $R^1R^2R^3N$ where each of $R^1$, $R^2$, and $R^3$ is independently a linear or branched alkyl group having from 1 to 4 carbon atoms the source of phosphorous comprises; a trialkyl phosphate of the formula $(R^4O)_3P=O$ where each $R^4$ is an alkyl group having from 1 to 4 carbon atoms.

2. The method of claim 1 wherein said alkylating agent comprises at least part of said source of phosphorus.

3. The method of claim 1 wherein said alkylating agent comprises an alkyl phosphate.

4. The method of claim 3 wherein said alkylating agent comprises a trialkyl phosphate.

5. A method of synthesizing an aluminophosphate or metalloaluminophosphate molecular sieve, the method comprising:
   (a) providing a synthesis mixture comprising water; a source of aluminum; an amine of the formula $R^1R^2R^3N$ where each of $R^1$, $R^2$, and $R^3$ is independently a linear or branched alkyl group having from 1 to 4 carbon atoms; a trialkyl phosphate of the formula $(R^4O)_3P=O$ where each $R^4$ is an alkyl group having from 1 to 4 carbon atoms, and optionally a source of a metal other than aluminum; and
   (b) maintaining said synthesis mixture under conditions sufficient to cause said trialkyl phosphate to react with said amine to produce a quaternary ammonium compound and to induce crystallization of said molecular sieve.

6. The method of claim 5 wherein said amine comprises triethylamine.

7. The method of claim 5 wherein $R^1$ and $R^2$ are independently selected from alkyl groups having from 1 to 3 carbon atoms and.

8. The method of claim 5 wherein each $R^4$ is a linear or branched alkyl group having from 1 to 4 carbon atoms.

9. The method of claim 8 wherein the trialkyl phosphate comprises triethyl phosphate.

10. The method of claim 5 wherein the molar ratio of amine to trialkylphosphate in the synthesis mixture is at least 3.

11. The method of claim 5 wherein the synthesis mixture comprises a source of silicon.

12. The method of claim 5 wherein the synthesis mixture comprises a source of phosphorus in addition to said trialkyl phosphate.

13. The method of claim 12 wherein said source of phosphorus comprises phosphoric acid.

14. The method of claim 5 wherein the synthesis mixture also contains seeds.

15. The method of claim 5 wherein said synthesis mixture comprises from about 0.01 ppm by weight to about 10,000 ppm by weight of seeds.

16. The method of claim 5 wherein said synthesis mixture comprises from about 100 ppm by weight to about 5,000 by weight of seeds.

17. The method of claim 5 wherein said conditions include a temperature of about 120° C. to about 220° C. for a time of about 4 hours to about 240 hours.

18. The method of claim 5 wherein said molecular sieve comprises a CHA framework type material.

19. A catalyst composition comprising a crystalline aluminophosphate or silicoaluminophosphate molecular sieve including a CHA framework-type material produced by the method of claim 18.

20. A process for producing olefins comprising contacting an organic oxygenate compound under oxygenate conversion conditions with the catalyst composition of claim 19.

21. A method of synthesizing an aluminophosphate or metalloaluminophosphate molecular sieve, the method comprising:

(a) providing a synthesis mixture comprising water; a source of aluminum; an amine of the formula $R^1R^2R^3N$ where each of $R^1$, $R^2$, and $R^3$ is independently an alkyl group or hydroxyalkyl group having from 1 to 8 carbon atoms; a trialkyl phosphate of the formula $(R^4O)_3P=O$ where each $R^4$ is an alkyl group having from 1 to 4 carbon atoms, and optionally a source of a metal other than aluminum, and wherein the molar ratio of amine to trialkylphosphate in the synthesis mixture is at least 3; and (b) maintaining said synthesis mixture under conditions sufficient to cause said trialkyl phosphate to react with said amine to produce a quaternary ammonium compound and to induce crystallization of said molecular sieve.

22. The method of claim 21 wherein each of $R^1$, $R^2$, and $R^3$ is independently a linear or branched alkyl group having from 1 to 4 carbon atoms.

23. The method of claim 21 wherein said amine comprises triethylamine.

24. The method of claim 21 wherein $R^1$ and $R^2$ are independently selected from alkyl and hydroxyalkyl groups having from 1 to 3 carbon atoms and $R^3$ is selected from 4- to 8-membered cycloalkyl groups optionally substituted by 1 to 3 alkyl groups having from 1 to 3 carbon atoms.

25. The method of claim 21 wherein said amine comprises N,N-dimethylcyclohexylamine.

26. The method of claim 21 wherein each $R^4$ is a linear or branched alkyl group having from 1 to 4 carbon atoms.

27. The method of claim 21 wherein the trialkyl phosphate comprises triethyl phosphate.

28. The method of claim 21 wherein the synthesis mixture comprises a source of silicon.

29. The method of claim 21 wherein the synthesis mixture comprises a source of phosphorus in addition to said trialkyl phosphate.

30. The method of claim 29 wherein said source of phosphorus comprises phosphoric acid.

31. The method of claim 21 wherein the synthesis mixture also contains seeds.

32. The method of claim 21 wherein said synthesis mixture comprises from about 0.01 ppm by weight to about 10,000 ppm by weight of seeds.

33. The method of claim 21 wherein said synthesis mixture comprises from about 100 ppm by weight to about 5,000 by weight of seeds.

34. The method of claim 21 wherein said conditions include a temperature of about 120° C. to about 220° C. for a time of about 4 hours to about 240 hours.

35. The method of claim 21 wherein said molecular sieve comprises a CHA framework type material.

36. A catalyst composition comprising a crystalline aluminophosphate or silicoaluminophosphate molecular sieve including a CHA framework-type material produced by the method of claim 35.

37. A process for producing olefins comprising contacting an organic oxygenate compound under oxygenate conversion conditions with the catalyst composition of claim 36.

* * * * *